United States Patent
Palumbo et al.

(10) Patent No.: US 6,855,326 B2
(45) Date of Patent: Feb. 15, 2005

(54) SKIN PROTECTION COMPOSITION

(75) Inventors: Gianfranco Palumbo, Bad Homburg (DE); Mario Guarracino, Silvi Marina (IT)

(73) Assignee: The Procter & Gamble Company, Cincinnati, OH (US)

( * ) Notice: Subject to any disclaimer, the term of this patent is extended or adjusted under 35 U.S.C. 154(b) by 162 days.

(21) Appl. No.: 10/251,296

(22) Filed: Sep. 20, 2002

(65) Prior Publication Data

US 2003/0035785 A1 Feb. 20, 2003

Related U.S. Application Data

(63) Continuation of application No. 09/555,169, filed as application No. PCT/US98/24692 on Nov. 20, 1998.

(30) Foreign Application Priority Data

Nov. 26, 1997 (EP) .............................................. 97120698

(51) Int. Cl.$^7$ .......................... A01N 25/34; A61K 7/00; A61F 13/00
(52) U.S. Cl. ....................... 424/402; 424/401; 424/443; 424/449; 604/368

(58) Field of Search ................................ 424/402, 401, 424/443, 449; 604/368

(56) References Cited

U.S. PATENT DOCUMENTS 3,091,241 A * 5/1963 Kellett et al. ............... 604/286
3,964,486 A    6/1976 Blaney

* cited by examiner

*Primary Examiner*—Gollamudi S. Kishore
*Assistant Examiner*—Isis Ghali
(74) *Attorney, Agent, or Firm*—Ian S. Robinson; Ken K. Patel; Steven W. Miller

(57) ABSTRACT

The invention relates to cationic compounds and triester compounds to be used for preparation of compositions, which preferably can be in the form of lotions, creams, powders, oils, foams and the like, and be applied to the skin to prevent or reduce or treat skin rash or diaper rash resulting from lypolytic dermatitis. The compositions of the invention can also be applied to diapers, incontinent-pads, wipes and the like. The invention also relates to the use of such a composition to prevent or reduce such a skin rash and a process for reducing the enzyme activity enzymes which are deactivated when the pH is reduced, such as lipase enzymes present on external skin.

18 Claims, No Drawings

SKIN PROTECTION COMPOSITION

CROSS REFERENCE

This is a continuation under 35 U.S.C. §120 of patent applications Ser. No. 09/555,169, filed May 25, 2000, which claims priority under 35 U.S.C. §371 to PCT International Application Serial No. PCT/US98/24692, filed Nov. 20, 1998; which claims priority to European Patent Application No. 97120698.2, filed Nov. 29, 1997.

The invention relates to cationic compounds and triester compounds to be used for preparation of compositions, which preferably can be in the form of lotions, creams, powders, oils, foams and the like, and be applied to the skin to prevent or reduce or treat skin rash or diaper rash resulting from lipolytic dermatitis. The compositions of the invention can also be applied to diapers, incontinent-pads, wipes and the like.

The invention also relates to the use of such a composition to prevent or reduce such a skin rash and a process for reducing the enzyme activity enzymes which are deactivated when the pH is reduced, such as lipase enzymes present on external skin.

BACKGROUND

Skin rash caused by dermatitis, often referred to as diaper rash, has always been a problem encountered by the users of disposable absorbent articles, such as diapers, incontinence articles, sanitary towels, training pants etc. Therefore, one of the biggest needs for these users is a solution to this type of skin rash problem.

The main factor which influences the development of skin rash is the contact of the skin with the wet body exudates, directly or for example contained in the absorbent article. Especially when the water content is high, skin rash can occur easily.

Manufacturers of diapers and skin care products have developed various products over the past decades which help reduce the occurrence of diaper rash (or skin rash).

The main focus thereby has been to reduce the exposure of the skin to the body exudates. This is for example done by introduction to the diaper of absorbing or better absorbing materials. The amount of water which is in contact with the skin is thus reduced.

Other products which are developed to address the skin-rash problem reduce the exposure of the skin to certain ingredients of the body exudates. An example of such ingredients of the exudate are bacteria which can infect the skin and thus start off or aggravate the skin rash.

For example, lotions have been developed which can form a barrier between the skin and the body exudates. Also, anti-inflammatory compositions can be applied to the skin or absorbent article.

EP 0191128 discloses a preparation comprising 8-hydroxy quinoline sulphate for treatment of skin irritation.

However, still one of the most heard complaints amongst users of absorbent articles such as diapers is the persistence of skin or diaper rash, despite the numerous products on the market which can be applied to prevent diaper or skin rash.

It has been discovered that yet another factor can set off or aggravate skin rash, namely the presence in the body exudate of various enzymes, especially lipase and protease enzymes.

EP 0117632B relates to disposable articles which comprise lipase inhibiting agents, preferably zinc containing components, and a vehicle material. Also mentioned is the use of glyceryl triacetate When the skin is exposed to lipase enzymes, the lipids of the skin can be affected by these enzymes. Furthermore, the protease enzymes present in the body exudate on the skin can affect the proteins (or peptides) of the skin. The protection or barrier function of the top layer of the skin (the Strateum Corneum) will thus be diminished. This can effect the health of the skin and/or facilitate the infection of the skin. This can thus lead to skin or diaper rash.

It has been found that triester compounds similar to lipids or the lipids of the skin in particular can function as enzyme substrates, which, when acted upon by a hydrolysing esterase enzyme, such as lipase enzymes, will be hydrolysed resulting in the release of free acids. Firstly, the presence of these acids will lower the pH of the area where the esters where topical applied to. This will amount to inactivation of all or most enzymes present in this area, in the body exudates, such as the lipase enzymes, protease enzymes. Secondly, the esterase or lipase enzymes are 'de-activated', because rather than hydrolysing the esters, such as lipids, of the skin, they hydrolyse the alternative substrate, the triester compounds of the invention.

It is known that bile salts are present in the body exudates. These bile salts are known to emulsify the lipase enzymes in the body, which ensures that the lipase enzymes are capable of performing on the lipid-water interface. It has been found that these bile salts still have an emulsifying function once outside the body, in the body exudates. They aid the lipase enzyme which is present in the body exudate by attacking the lipids in the outer layer skin, exposed to the body exudate.

The inventors have found that these bile salts can be inactivated (and thereby the lipase can be deactivated) when the bile salts are reacted with specific cationic compounds. They have found that the compositions comprising the cationic compounds can thereto be applied directly to the skin. This can be done by introduction of the composition into a cosmetic cream, lotion, oil, powder. Alternatively, the composition can be applied to an absorbent article, such as a diaper, which then can be applied to the skin.

Surprisingly it has been found that the use of a combination of the cationic compounds and the triester compounds has an enhanced and elongated effect on the skin-rash or lipolytic dermatitis. Unexpectingly, it has been found that the inhibition or inactivation of the lipase enzymes by the inactivation of the bile salts by the cationic compounds does not make the triester compounds less useful as enzyme substrates. Namely, it has been found that the cationic compounds provide an immediate effect, i.e. inhibition or inactivation of the lipase enzymes, which may reduce over time, whilst the effect of the triester compounds is relatively delayed but long-lasting. Thus, the combination of the two compounds provides an very effective, immediate and long-lasting reduction or prevention of the diaper/skin rash, resulting from dermatitis caused by the enzymes present on the body exudates on the skin.

SUMMARY OF THE INVENTION

The invention relates to the use of a compound (a) and a compound (b) for preparation of a composition for prevention, reduction or treatment of lipolytic dermatitis of the external skin, wherein (a) and (b) are:

(a) a triester compound of the formulation:

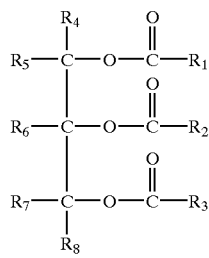

(I)

wherein $R_1$, $R_2$ and $R_3$ are independently an alkyl or alkenyl or hydroxyalkyl group with from 1 to 22 carbon atoms, and $R_4$, $R_5$, $R_6$, $R_7$ and $R_8$ are independently selected from the group consisting of $C_1$–$C_{10}$ linear or branched alkyl, alkenyl or hydroxyalkyl groups, hydroxy, chloride, bromide, amine or hydrogen; and (b) a cationic compound of the formulation:

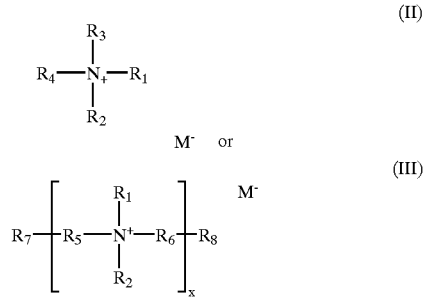

(II)

(III)

or an amphoteric compound and preferably an acidity source, the amphoteric compound having at its iso-electric point the formula:

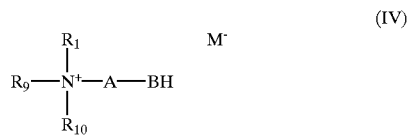

(IV)

wherein $R_1$, $R_2$, $R_3$ and $R_4$ are independently selected from the group consisting of $C_1$–$C_{22}$ linear or branched alkyl, alkenyl, aryl, arylalkyl, amidoalkyl, (poly) alkoxy, hydroxyalkyl, or acyl groups, or two or more groups of $R_1$, $R_2$, $R_3$ and $R_4$ form together one or more ring structures; $R_5$, $R_6$ and A are independently selected from the group consisting of $C_1$–$C_{22}$ linear or branched alkylene, alkenylene, (poly) alkoxylene, hydroxyalkylene, arylalkylene or amido alkylene groups; $R_7$ and $R_8$ are independently an $C_1$–$C_4$ alkyl, alkenyl, alkoxy group or a hydroxy group or hydrogen; $R_9$ and $R_{10}$ are independently selected from the group consisting of $C_1$–$C_{22}$ linear or branched alkenyl, aryl, arylalkyl, amidoalkyl, (poly) alkoxy, hydroxyalkyl, or acyl groups, or two or more of the groups $R_1$, $R_9$ and $R_{10}$ form together one or more ring structures; BH is a proton donating group; x is from 2 to 4; and M– is a counter ion.

The invention also provides a disposable absorbent article, preferably a diaper or wipe, containing a composition which comprises the cationic compound and ester compound as described above, preferably at such a level that the compounds are each present at a level of from 0.01% to 10% by weight of the article, preferably comprised in the topsheet of the diaper.

The invention also provides compositions introduced into a cosmetic cream, lotion, gel, oil, ointment or powder and the like, for topical application to the external skin.

DETAILED DESCRIPTION OF THE INVENTION

The cationic compounds and triester compounds are used in for the preparation of compositions for prevention, reduction or treatment of lipolytic dermatitis of the (external) skin.

By treatment or reduction is meant herein the reduction of the lipolytic dermatitis or the rash of the skin, or diaper rash, which is caused by the lipase enzymes present on the skin, or at least stabilising the dermatitis or rash of the skin which is caused by these enzymes.

The composition of the invention can be applied to the skin which is in contact with at least the lipase enzymes. Such compositions can be comprised in a cream, lotion, oil, ointment, foam, powder or gel, which can be topical applied to the skin.

Alternatively, the compositions of the invention can be applied to an absorbent article, which can be brought in close contact with the skin which is in contact with the lipase enzymes. Such articles are preferably disposable articles such as diapers, incontinent pads, training pants, sanitary towels, feminine hygiene garments, wet and dry wipes.

By the term "topical application" or "topical(ly) applied", as used herein, is meant directly laying on or spreading on epidermal tissue, especially outer skin.

The amount of the composition comprising the ester compounds of the invention will vary with the particular location of the condition being treated, the severity of the condition being treated, the expected duration of the treatment, any specific sensitivity to either the composition itself, or the concentration of the ester compounds specific to the user, the condition of the user, concurrent therapies being administered, other conditions present in the user.

For the present invention it is preferred that a minimum inhibitory concentration of the compositions containing the ester and cationic compounds of the invention is topically applied, to act as lipase de-activator or inhibitor to the area in need of treatment of the lypolytic dermatitis or the area where prevention of enzymatic dermatitis is desired in a form such that it is available to inhibit the activity of the lipase present.

This area (or "affected area", as used herein) is meant the area of the skin which is presently exhibiting any levels of skin rash or enzymatic dermatitis, or the area which will be in prolonged contact with body exudates containing the enzymes, in particular the lipase enzyme. This also includes the area immediately proximate to the described area. It is the area at which treatment, reduction of, and/or prevention is desired.

Lipolytic Dermatitis

This invention deals with compositions comprising the triester compounds and cationic compounds described above (or (disposable) absorbent articles incorporating the compositions) for the treatment of dermatitis, in particular diaper rash or diaper dermatitis caused by the lipase enzymes present in the body exudates (thus lipolytic dermatitis) and other conditions which are associated with prolonged contact of the skin with body exudates and/or the wearing of a absorbent article, or in particular a diaper.

Lipase, lipase enzyme or lipolytic enzyme is the trivial or common term employed to represent a group of enzymes belonging to the esterases. Their general activity is to hydrolyse fats present in the ester form (such as the glycerides found in human skin), and accordingly generate fatty acids and glycerol. Because this group of enzymes is so widely distributed in plants, moulds, bacteria, milk, and milk-products, as well as in almost all animal tissues, and because moreover human lipase enzymes are present in the pancreatic exudates, they are almost always present in body exudates.

The activity of lipase enzymes contributes to almost all skin rash, or in particular diaper rash, causing irritation by the digestive degenerative action of these enzymes on the skin per se and by breaking down the lipid-skin components, compromises the barrier property of the skin in the affected area. This breakdown of the integrity of the skin allows other components of the body exudates (urine and faeces in particular), which may not, by themselves, be irritating, to migrate through the compromised skin. At this point normally harmless components may then become irritating.

Compositions

Triester Compounds

The present invention provides triester compounds, as defined above in formulation (I) and cationic compounds as defined above in formulations (II), (III), and (IV) for use in the preparation of compositions which can be used for treatment, prevention or reduction of the skin rash or particularly diaper rash, which is set off or aggravated by enzymes, in particular the esterase enzymes, lipase, and protease enzymes, thus being the result of enzymatic dermatitis.

The composition preferably comprise the triester compounds at a level of from 0.01% to 90%, more preferably from 0.5% to 60%, most preferably from 2% to 25% by weight of the composition.

It should be understood that for the purpose of this invention, the groups $R_1$–$R_8$ of formulations (I) and groups $R_1$–$R_{10}$ of formulations (II), (III) and (IV) above can be substituted by any appropriate substituent group.

Preferred triester compounds have one or more, preferably all of $R_4$, $R_5$, $R_6$, $R_7$ and $R_8$ of said compound being hydrogen.

Preferably, the triester compounds has at least one, preferably all of $R_1$, $R_2$ and $R_3$ being C1–C4 alkyl groups.

It can be highly preferred that the triester compound is glycerol triacetate.

Cationic Compound

In the formulations (II), (III) and (IV) above, $R_1$, $R_2$, $R_3$ and $R_9$ are independently preferably $C_1$–$C_8$, more preferably $C_1$–$C_4$ alkenyl or alkoxy, more preferably alkyl groups, most preferably methyl or ethyl groups.

Preferably, $R_4$, $R_5$ and $R_{10}$ are independently $C_8$–$C_{18}$, more preferably $C_{12}$–$C_{16}$ alkenyl or alkoxy, more preferably alkyl or arylalkyl groups, whereby it can be preferred that one of the $R_4$, $R_5$ and $R_9$ substituents is benzyl group.

Alternatively, it can be preferred that the cationic compound comprises at least one $R_1$, $R_2$ or $R_3$ or $R_9$ being a poly alkoxy group. Thus, $R_1$, $R_2$, $R_3$ and $R_9$ preferably are independently polyalkoxy groups comprising $C_2$–$C_6$, preferably $C_2$–$C_3$ alkoxy units and having an alkoxylation number of from 2 to 50, preferably from 5 to 18. Then, $R_3$, $R_4$ and $R_{10}$ are independently preferably $C_1$–$C_8$, more preferably $C_1$–$C_4$ alkenyl or alkoxy, more preferably alkyl groups, most preferably methyl or ethyl groups.

A, $R_5$ and $R_6$ are, independently, preferably $C_1$–$C_6$ alkenylene or more preferably alkylene groups, most preferably methylene or ethylene.

Preferred compounds can be benzalkonium chloride or Merquat 2200 (Trade name, being a 2-Propeneamide polymer of N,N-dimethyl-N-2-Propenyl-1-amonium chloride).

Preferred cationic compounds of the formulas above comprise one or more substituted $R_1$, $R_2$, $R_3$, $R_4$, $R_9$ or $R_{10}$ groups and/or a substituted $R_5$ and/or substituted $R_6$ group, whereby the substituent is selected from the group from the group consisting of derivatives of silicon, glucose, fructose and saccharose. Preferred can be Glucquat 125 (trade name, being lauryl dimethyl glucet-10-hydroxydimonium chloride).

Preferred cationic compounds of the formula (III) above are betaine or sulpho betaine having preferably $R_1$ and $R_9$ being a methyl group.

The composition preferably comprise the cationic compounds at a level of from 0.01% to 90%, more preferably from 0.5% to 60%, most preferably from 2% to 25% by weight of the composition.

Lotions, Creams, Oils, Ointments, Foams, Gels, Powders and the Like

The compositions in accordance with the invention can be cosmetic compositions, preferably in the form of lotions, creams, oils, foams, ointments, powders, gels and the like. They can comprise any of the ingredients commonly used in the art for such compositions.

It is to be understood that the ingredients of the compositions above will depend on the character of the composition, thus lotions will generally comprise different additional ingredients than powders.

In the cosmetic creams, lotions, gels, oils or powders comprising the composition of the invention preferably an acidity source is present, preferably such that is capable to reduce the pH of the skin to below a pH of 8, more preferably below a pH of 7, more preferably below a pH of 6, or even more preferred below a pH of 5.

A wide variety of optional ingredients such as non-occlusive moisturisers, humectants, gelling agents, neutralising agents, perfumes, colouring agents, can be added to the skin compositions herein.

It can be preferred that the cosmetic cream, lotion, gel, oil, ointment or powder are substantially free from nonionic and/or anionic surfactants and/or phosphoric acid esters and/or enzymes.

Additional Ingredients

The composition of the invention can comprise additional ingredients. Which ingredient are present and in which level depends on the character of the composition and the use thereof.

A highly preferred additional component to be used for the preparation of the compositions of the present invention or for use in the compositions of the present invention are certain additional ester compounds.

A highly preferred additional ester compound for use in, or for preparation of the compositions of the invention is of the formulation:

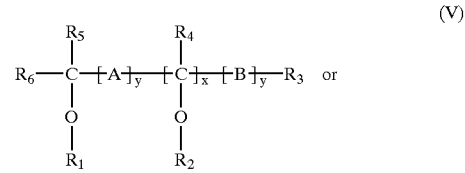

(V)

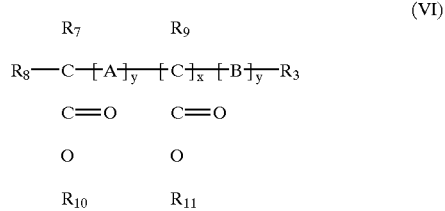

for preparation of a composition for prevention or treatment of enzymatic dermatitis wherein $R_1$ and each $R_2$ independently are an acyl group with from 2 to 22 carbon atoms, or an alkyl, alkenyl, arylalkyl, hydroxyalkyl group with from 1 to 24 carbon atoms or hydrogen, whereby at least one of $R_1$ and $R_2$ is such an acyl group, $R_3$ $R_4$, $R_5$, $R_6$, $R_7$, $R_8$, and $R_9$ are independently an alkyl, alkenyl, arylalkyl, hydroxyalkyl, alkoxy groups of from 1 to 24 carbon atoms, hydroxy group or hydrogen; $R_{10}$ and $R_{11}$ are independently an alkyl, alkenyl, arylalkyl, hydroxyalkyl, alkoxy groups of from 2 to 24 carbon atoms, hydroxy group or hydrogen; A and B are independently a $C_1$–$C_6$ linear or branched alkylene, alkenylene, alkoxylene, hydroxyalkylene groups; the values of x are independently from 0 to 15; the values of y are independently 0 or 1, with the proviso that when x=2 and y=0, at least one $R_2$ is an alkyl, alkenyl, arylalkyl, hydroxyalkyl group with from 1 to 24 carbon atoms or hydrogen It should be understood that for the purpose of this invention, the groups $R_1$–$R_{11}$ of formulations (V) and (VI) above can be substituted by any appropriate substituent group.

Preferred are the ester compounds as defined above, wherein the compound is of formula (V) or (VI) wherein x is 1 or 2, y is 0; $R_1$ and one $R_2$ are a $C_2$–$C_{16}$ acyl group, $R_{10}$ and one or more $R_{11}$ are a $C_2$–$C_{16}$ alkyl group; $R_3$, $R_4$, $R_5$, $R_6$, $R_7$ and $R_8$ are hydrogen It is highly preferred that the additional ester compound is a mono or diester of formula (VI), most preferably a mono or diester of citric acid or tartaric acid (or salts thereof), or a triester of citric acid.

The additional ester compounds are preferably present in the compositions of the invention at a level of from 0.01% to 20%, more preferably from 0.05% to 10%, most preferably from 0.1% to 5% by weight of the composition.

Process

Also encompassed in the invention is a process for reducing the enzyme activity of the enzymes present on the external skin, whereby the process comprises the steps of preferably topical applying a composition according to the invention to the external skin.

Thereby, acids are formed (in situ), preferably capable of reducing the initial pH to below 7.9, more preferably below 7.5 or even 7.3.

It can be preferred that an additional acidity source is present, capable of reducing the pH to below 7.3, preferably below 6 or even 5.

The composition used in the process or the process is preferably such that within the first 15 minutes after application of the composition to the affected area, the lipase enzyme activity is reduced to 35%, preferably 25%, more preferably less than 20% of the initial lipase activity in this area.

Preferably the composition used in the process or the process is such that 60 minutes after application of the composition to the affected area, the lipase enzyme activity is still less than 45%, preferably 35%, more preferably less than 30% of the initial lipase activity in this area.

This process can be preferably done by applying an absorbent article which comprises the composition present in a suitable level, to the skin.

Absorbent Articles

The compositions of the invention, comprising the triester compounds and the cationic compound, can be comprised in a absorbent article, preferably a disposable absorbent article. A particularly preferred absorbent articles therefor is a diaper, which preferably comprises the composition in the topsheet of the diaper.

As used herein, the term "absorbent articles" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

The structure of the disposable absorbent article is not critical to the practice of the present invention.

Normally, the composition is incorporated into the absorbent article or diaper in particular in an amount which will deliver the required treatment or reduction or prevention of the lipolytic dermatitis preferably after frequent use.

The disposable absorbent article preferably contains the cationic compounds and the triester compounds in a compositions present at a level of from 0.01% to 30%, more preferably from 0.01% to 10%, most preferably from 0.05% to 5% by weight of the article.

An absorbent article generally comprises
 an absorbent core (which may consist of sub-structures);
 a fluid pervious topsheet;
 a fluid impervious backsheet;
 optionally further features like closure elements or elastification.

As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

A preferred wipe for the purpose of this invention comprises an absorbent fibrous material or core into which the composition may be releasably incorporated. A highly preferred disposable wipe for the purposes of this invention comprises an absorbent fibrous material and a faeces-impermeable backing material; said backing being super-posed or co-extensive with one face of said absorbent fibrous material; said backing material most preferably being a web-backing material and most preferably having a width greater than said absorbent material providing side marginal portions which extend beyond said absorbent material, said margin portions being folded around and on top of the edges of said absorbent material. The compositions of the invention agent may be releasably incorporated into the wipe structure by diverse methods which will be readily apparent to those skilled in the art. For example, the compositions can be present in aqueous or volatile carrier such as water, ethanol, or the like, or creams, lotions, oils, ointments, gels or powders, and applied to the absorbent material by spraying, dipping, printing, soaking or otherwise contacting the absorbent material of the wipe with the lipase-inhibiting agent and its carrier. A skin cleansing agent, preferably an oleaginous cleansing agent, may optionally be releasably incorporated into the absorbent material as well.

The compositions of the present invention are preferably incorporated into a diaper, preferably into the absorbent core structure or most preferably into the topsheet structure. The composition may be incorporated into the diaper structure by diverse methods which will be readily apparent to those skilled in the art. For example, the composition can be, optionally after being dispersed aqueous or volatile carrier such as water, ethanol, or the like, applied to the diaper topsheet, to the absorbent core, or to the core side of the backsheet, by spraying, dipping, printing, soaking or otherwise contacting the selected structural element of the diaper with composition and optionally its carrier, which is called herein impregnation.

The diaper preferably comprises a liquid pervious topsheet, a liquid impervious backsheet joined with the topsheet, an absorbent core positioned between the topsheet and the backsheet. While the topsheet, the backsheet, and the absorbent core may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991.

The backsheet is positioned adjacent the garment surface of the absorbent core and is preferably joined thereto by attachment means such as those well known in the art. For example, the backsheet may be secured to the absorbent core by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The absorbent article may further comprise elastification or closure features well-known in the art and—for example—described in E 0254476 (Alemany).

The topsheet is positioned adjacent the body surface of the absorbent core and is preferably joined thereto and to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

Generally, the topsheet is compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibres (e.g., wood or cotton fibres), synthetic fibres (e.g., polyester or polypropylene fibres), or a combination of natural and synthetic fibres. There are a number of manufacturing techniques which may be used to manufacture the topsheet. For example, the topsheet may be a nonwoven web of fibres spunbonded, carded, wet-laid, meltblown, hydroentangled, combinations of the above, or the like.

Preferably the topsheet comprises a means to adjust hydrophilicity of the material.

Absorbent cores comprise essentially all absorbent parts of the absorbent article other than the topsheet, which contribute to fluid absorbency or fluid handling.

The absorbent cores should be generally compressible, conformable, non-irritating to the wearer's skin, and capable of absorbing and retaining liquids such as urine and other certain body exudates.

The absorbent core can be made of a variety of materials. Preferred materials are fibrous materials, which can form a fibrous web, natural occuring or synthetic fibres or optionally thermoplastic fibres. In addition thereto polymeric stiffening agents are preferably present. Also preferred can be hydrogel-forming polymers or absorbent polymers.

The various core, topsheet and backsheet materials can be arranged in any way known in the art, such as described in Weisman et al. (EP 0 202 125) or Alemany et al. (EP 0 254 476).

Also encompassed in the present invention is a process for making a diaper comprising the composition of the invention whereby the topsheet is impregnated with the composition before incorporation in the diaper.

What is claimed is:

1. A composition for the reduction of lipase enzyme activity on skin, said composition comprising:

(a) a compound of the formulation:

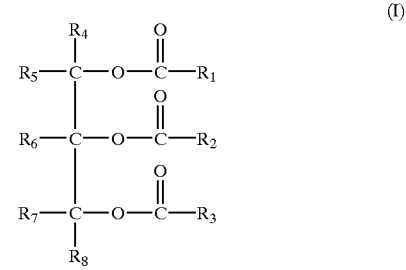

wherein $R_1$, $R_2$ and $R_3$ are independently an alkyl or alkenyl or hydroxyalkyl group with from 1 to 22 carbon atoms, and $R_4$, $R_5$, $R_6$, $R_7$ and $R_8$ are independently selected from the group consisting of $C_1$–$C_{10}$ linear or branched alkyl, alkenyl or hydroxyalkyl groups, hydroxy, chloride, bromide, amine or hydrogen; and (b) a compound of the formulation:

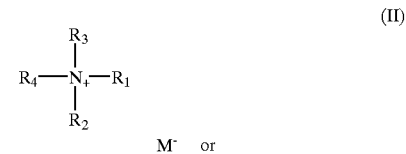

-continued

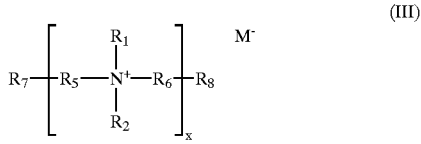
(III)

an amphoteric compound, said amphoteric compound having at its iso-electric point the formula:

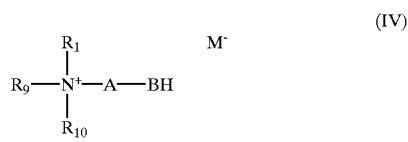
(IV)

wherein $R_1$, $R_2$, $R_3$ and $R_4$ are independently selected from the group consisting of $C_1$–$C_{22}$ linear or branched alkyl, alkenyl, aryl, arylalkyl, amidoalkyl, (poly) alkoxy, hydroxyalkyl, or acyl groups, or two or more groups of $R_1$, $R_2$, $R_3$ and $R_4$ form together one or more ring structures; $R_5$, $R_6$ and A are independently selected from the group consisting of $C_1$–$C_{22}$ linear or branched alkylene, alkenylene, (poly) alkoxylene, hydroxyalkylene, arylalkylene or amido alkylene groups; $R_7$ and $R_8$ are independently an $C_1$–$C_4$ alkyl, alkenyl, alkoxy group or a hydroxy group or hydrogen; $R_9$ and $R_{10}$ are independently selected from the group consisting of $C_1$–$C_{22}$ linear or branched alkyl, alkenyl, aryl, arylalkyl, amidoalkyl, (poly) alkoxy, hydroxyalkyl, or acyl groups, or two or more of the groups $R_1$, $R_9$ and $R_{10}$ form together one or more ring structures; BH is a proton donating group; x is from 2 to 4; and M– is a counter ion; and wherein said composition within the first 15 minutes of application of said composition to an affected area, reduces the lipase enzyme activity to 35% of initial lipase activity in said affected area.

2. The composition according to claim 1 wherein said compound (a) has $R_4$, $R_5$, $R_6$, $R_7$ and $R_8$ being hydrogen.

3. The composition according to claim 1 wherein said compound (a) has $R_1$, $R_2$ and $R_3$ being independently a C1–C4 alkyl group.

4. The composition according to claim 3 wherein said compound (a) is glycerol triacetate.

5. The composition according to claim 1 wherein said cationic compound (b) comprises one or more substituted $R_1$, $R_2$, $R_3$, $R_4$, $R_9$ or $R_{10}$ groups and/or a substituted $R_5$ and/or substituted $R_6$ group, whereby the substitute is selected from the group consisting of derivatives of silicon, glucose fructose and saccharose.

6. The composition according to claim 1 wherein said cationic compound (b) comprises at least one of $R_1$, $R_2$, $R_3$ and $R_9$ being $C_1$–$C_8$ alkyl group.

7. The composition according to claim 1 wherein said cationic compound (b) comprises at least one of $R_1$, $R_2$ or $R_3$ or $R_9$ being a poly alkoxy group.

8. The composition according to claim 1 wherein said cationic compound (b) is of formula (IV), being a betaine compound or sulphobetaine compound.

9. The composition according to claim 1 wherein said composition is in the form of a cosmetic cream, lotion, gel, oil, ointment or powder.

10. The composition according to claim 1 wherein said composition within the first 15 minutes of application of said composition to an affected area, reduces the lipase the lipase enzyme activity to 25% of initial lipase activity in said affected area.

11. The composition according to claim 10 wherein said composition within the first 15 minutes of application of said composition to an affected area, reduces the lipase enzyme activity is reduced to less than 20% of initial lipase activity in said affected area.

12. The composition according to claim 1 wherein said composition further comprises:

(c) an ester of the formula:

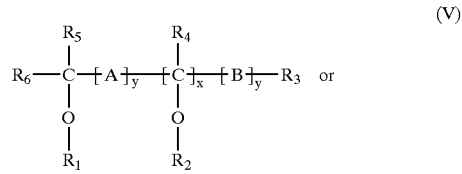
(V)

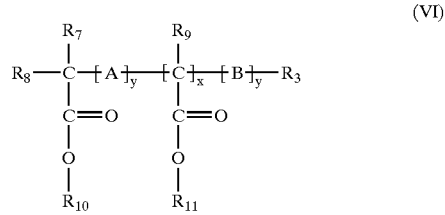
(VI)

wherein $R_1$ and each $R_2$ independently are an acyl group with from 2 to 22 carbon atoms, or an alkyl, alkenyl, arylalkyl, hydroxyalkyl group with from 1 to 24 carbon atoms or hydrogen, whereby at least one of $R_1$ and $R_2$ is such an acyl group; $R_3$, $R_4$, $R_5$, $R_6$, $R_7$, $R_8$, and $R_9$ are independently an alkyl, alkenyl, arylalkyl, hydroxyalkyl, alkoxy groups of from 1 to 24 carbon atoms, hydroxy group or hydrogen; $R_{10}$ and $R_{11}$ are independently an alkyl, alkenyl, arylalkyl, hydroxyalkyl, alkoxy groups of from 2 to 24 carbon atoms, hydroxy group or hydrogen; A and B are independently a $C_1$–$C_6$ linear or branched alkylene, alkenylene, alkoxylene, hydroxyalkylene groups; the values of x are independently from 0 to 15; the values of y are independently 0 or 1, with the proviso that when x=2 and y=0, at least one $R_2$ is an alkyl, alkenyl, arylalkyl, hydroxyalkyl group with from 1 to 24 carbon atoms or hydrogen.

13. The composition according to claim 1 wherein said composition is substantially free of nonionic surfactants and anionic surfactants.

14. The composition according to claim 1 wherein said composition is substantially free of phosphoric acid esters.

15. A disposable absorbent article in the form of a wet-wipe, wipe, diaper or catamenial article for use on or application to the external skin containing a composition according to claim 1.

16. A dipsosable absorbent article according to claim 15 wherein said disposable absorbent article is a diaper and said compound (a) and said compound (b) are present at a level of from about 0.01% to about 10% by weight of the diaper.

17. A disposable diaper according to claim 16 whereby the diaper comprises a topsheet which contains the composition.

18. A method for reducing the lipase enzyme activity in an affected area comprising the steps of administering to said affected area of a subject a composition comprising:

(a) a compound of the formulation:

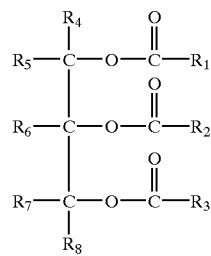

(I)

wherein $R_1$, $R_2$ and $R_3$ are independently an alkyl or alkenyl or hydroxyalkyl group with from 1 to 22 carbon atoms, and $R_4$, $R_5$, $R_6$, $R_7$ and $R_8$ are independently selected from the group consisting of $C_1$–$C_{10}$ linear or branched alkyl, alkenyl or hydroxyalkyl groups, hydroxy, chloride, bromide, amine or hydrogen; and (b) a compound of the formulation:

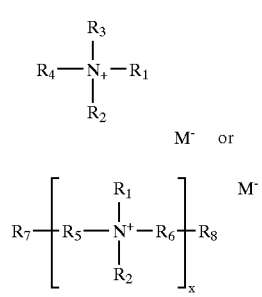

(II)

or (III)

an amphoteric compound, said amphoteric compound having at its iso-electric point the formula:

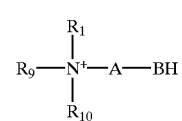

(IV)

wherein $R_1$, $R_2$, $R_3$ and $R_4$ are independently selected from the group consisting of $C_1$–$C_{22}$ linear or branched alkyl, alkenyl, aryl, arylalkyl, amidoalkyl, (poly) alkoxy, hydroxyalkyl, or acyl groups, or two or more groups of $R_1$, $R_2$, $R_3$ and $R_4$ form together one or more ring structures: $R_5$, $R_6$ and A are independently selected from the group consisting of $C_1$–$C_{22}$ linear or branched alkylene, alkenylene, (poly) alkoxylene, hydroxyalkylene, arylalkylene or amido alkylene groups; $R_7$ and $R_8$ are independently and $C_1$–$C_4$ alkyl, alkenyl, alkoxy group or a hydroxy group or hydrogen; $R_9$ and $R_{10}$ are independently selected from the group consisting of $C_1$–$C_{22}$ linear or branched alkyl, alkenyl, aryl, arylalkyl, amidoalkyl, (poly) alkoxy, hydroxyalkyl, or acyl groups, or two or more of the groups $R_1$, $R_9$ and $R_{10}$ form together one or more ring structures; BH is a proton donating group: x is from 2 to 4; and M– is a counter ion; and wherein said method within the first 15 minutes of application of said composition to said affected area, reduces said lipase enzyme activity to 35% of initial lipase activity in said affected area.

* * * * *